(12) United States Patent
Schaefer et al.

(10) Patent No.: US 9,221,854 B2
(45) Date of Patent: Dec. 29, 2015

(54) ISOMERIZATION OF OLEFINIC COMPOUNDS

(71) Applicant: BASF SE, Ludwigshafen (DE)

(72) Inventors: Bernd Schaefer, Dierbach (DE); Wolfgang Siegel, Limburgerhof (DE)

(73) Assignee: BASF SE (DE)

( * ) Notice: Subject to any disclaimer, the term of this patent is extended or adjusted under 35 U.S.C. 154(b) by 0 days.

(21) Appl. No.: 13/968,787

(22) Filed: Aug. 16, 2013

(65) Prior Publication Data

US 2014/0051889 A1 Feb. 20, 2014

Related U.S. Application Data

(60) Provisional application No. 61/684,146, filed on Aug. 17, 2012.

(51) Int. Cl.
*C07F 9/54* (2006.01)
(52) U.S. Cl.
CPC .................................. *C07F 9/5442* (2013.01)
(58) Field of Classification Search
USPC ................................................... 568/8, 9, 17
See application file for complete search history.

(56) References Cited

U.S. PATENT DOCUMENTS

| 4,134,922 A * | 1/1979 | Leeder ............................... 568/9 |
| 5,504,230 A | 4/1996 | John et al. |
| 2013/0166473 A1 | 6/2013 | Lutnick et al. |

FOREIGN PATENT DOCUMENTS

| DE | 2745729 A1 | 4/1978 |
| EP | 0659739 A1 | 6/1995 |
| WO | WO-99/09969 A1 | 3/1999 |
| WO | WO-2004089887 A1 | 10/2004 |
| WO | WO-2008037465 A1 | 4/2008 |
| WO | WO-2013068465 A2 | 5/2013 |
| WO | PCT/EP2013/066580 | 8/2013 |

OTHER PUBLICATIONS

Li; Journal of Organic Chemistry, 1982, 47, 4298-4303.*
International Search Report for PCT/EP2013/066580, mailing date Oct. 15, 2013.
Englert, G., et al., "Synthesis, Isolation, and Full Spectroscopic Characterization of Eleven (Z)-Isomers of (3R, 3'R)-Zeazanthin", Helvetica Chimica Acta, vol. 74, (1991), pp. 969-982.

* cited by examiner

*Primary Examiner* — Sudhakar Katakam
*Assistant Examiner* — Pancham Bakshi
(74) *Attorney, Agent, or Firm* — Drinker Biddle & Reath LLP

(57) ABSTRACT

The present invention relates to a process for preparing an olefinically unsaturated phosphonium salt having at least two olefinic double bonds, of which one double bond has a Z or cis conformation and the second or a further double bond an E conformation, from an olefinically unsaturated phosphonium salt having at least two olefinic double bonds of different configuration compared to the target compound, and both especially have an all-E or all-trans conformation. In addition, the invention provides for the use of the compound obtained by the process for provision of terpenoid substances as medicaments.

21 Claims, No Drawings

ISOMERIZATION OF OLEFINIC COMPOUNDS

CROSS-REFERENCE TO RELATED APPLICATIONS

This application claims the benefit of U.S. Provisional Application 61/684,146, filed Aug. 17, 2012, which is incorporated herein by reference.

The present invention relates to a process for preparing an olefinically unsaturated phosphonium salt 1 having at least two double bonds, the phosphonium salt 1 having Z configuration with respect to one double bond and E configuration with respect to the other or at least one further double bond. The present invention further comprises a wide variety of different uses of the phosphonium salt 1 prepared by the process according to the invention.

[(2Z,4E)-3-Methyl-5-(2,6,6-trimethylcyclohexen-1-yl) penta-2,4-dienyl]triphenylphosphonium salt 1 is a valuable synthesis unit for preparation of 9Z-carotenoids and 9Z-retinoids. For instance, 9Z-β-carotene is an intermediate in the biosynthesis of various phytohormones with different signaling action which will have beneficial future uses in crop protection. A prominent example is carlactone (Science 335 (2012) 1348). 9Z-Retinoic acid is a physiologically important compound (Nature 355 (1992) 359) which can also be used as an active pharmaceutical ingredient for treatment of various skin disorders (WO-A1-99/09 969), such as hand eczema and Kaposi's sarcoma.

An industrially employable synthesis for preparation of 9Z-retinoic acid was described for the first time in 1994 (EP-A1-0 659 739). In the process disclosed in this document a mother liquor of a C15-triarylphosphonium salt mixture is used, comprising the 2Z,4E-isomer 1 of said salt in enriched form, and this is reacted with β-formylcrotonic esters in a Wittig reaction.

As well as the 2Z,4E isomer 1, however, further isomers including the 2E,4E isomer (also referred to as the all-E isomer or as the all-trans isomer), the 2Z,4Z isomer and the 2E,4Z isomer of the C15-triarylphosphonium salt are present in a mother liquor and, so to speak, in the enriched mother liquor. Furthermore, for the 9Z-retinoic acid synthesis, use is made only of the mother liquor or of the enriched mother liquor, both of which, by definition, are obtained by or in a crystallization process of an isomer mixture of C15-triarylphosphonium salts. Accordingly, the isomer of the C15-triarylphosphonium salt obtained as a crystalline solid in the respective crystallization process is likewise unavailable for a further conversion to 9Z-retinoic acid.

The extent to which the phosphonium salt preparation gives rise to unwanted isomers of C15-triarylphosphonium hydrogensulfate which cannot be sent for further processing to give 9Z-retinoic acid is made clear by example 1 of the '739 document.

First of all, as already stated, crystals are no longer available as product of value since only the mother liquor is employed. This gives 91.8 g of oil from which, after removal of crystals which have precipitated in turn, 42.2 g of an enriched oil are obtained, comprising 28.03 g (65.8% by weight) of (2Z,4E)-3-methyl-5-(2,6,6-trimethylcyclohexen-1-yl)penta-2,4-dienyl]triphenylphosphonium salt of the formula 1 and 8.01 g (19% by weight) of [(2E,4E)-3-methyl-5-(2,6,6-trimethylcyclohexen-1-yl)penta-2,4-dienyl] triphenylphosphonium salt of the general formula 2. It can be seen that, from previously 91.8 g of oil obtained from mother liquor, only 28.03 g of 2Z,4E-isomer are obtained, corresponding to a yield of 30.5% by weight. Therefore, almost 70% by weight of oil remains unutilized from the previously 91.8 g of oil which was obtained from the mother liquor.

This loss is several times higher if the weight of C15-triarylphosphonium salt of the formula 1 obtained is based not just on the oil obtained from the mother liquor, but the total weight of the oil obtained from the mother liquor and the crystals removed by crystallization from the reaction mixture prior to workup is instead considered.

Example 2 of the '739 document shows similar results in conversion of a corresponding C15-triarylphosphonium chloride.

Regardless of these results, in WO-A1-2004/089887 too, exclusive use is made of a mother liquor as a source for (2Z,4E)-3-methyl-5-(2,6,6-trimethylcyclohexen-1-yl)penta-2,4-dienyl]-triphenylphosphonium salts, especially chlorides (see page 2 line 16 to page 3 line 9), and equally low yields are obtained thereby. For instance, example 1 shows that, from 200 g of an oil obtained from a mother liquor, only 62.06 g, corresponding to 31.0% by weight based on the amount of oil used, are obtained. Therefore, almost 70% by weight of an oil from the previously 200 g of oil used remain unutilized here too. In the same way, the loss here is also several times greater when the weight of C15-triarylphosphonium salt of the formula I is based not just on the oil obtained from the mother liquor, but on the total weight of the oil obtained from mother liquor and the crystals removed by crystallization from the reaction mixture prior to workup.

Even 14 years after filing of the '739 document, the mother liquor used in the documents already cited is still being employed as the source for the [(2Z,4E)-3-methyl-5-(2,6,6-trimethylcyclohexen-1-yl)penta-2,4-dienyl]triphenylphosphonium salt 1. For instance, example 1 of WO-A1-2008/037465 states that 300 g thereof should be used for this purpose and should be subjected to an extraction and crystallization. Ultimately, 69 g of the [(2Z,4E)-3-methyl-5-(2,6,6-trimethylcyclohexen-1-yl)penta-2,4-dienyl]triphenylphosphonium salt 1 are obtained with a purity of >97%. This corresponds to a yield of 23% based on the amount of mother liquor used and cannot be satisfactory with regard to economic viability of the reaction. If the yield is calculated not just on the basis of the amount of mother liquor used but of the total weight of mother liquor and previously obtained amount of crystals, the yield here too is worse by some way.

Obtaining [(2Z,4E)-3-methyl-5-(2,6,6-trimethylcyclohexen-1-yl)penta-2,4-dienyl]triphenylphosphonium salt 1 exclusively from mother liquors, and additionally in such small yields, makes it noticeably expensive to produce 9Z-retinoic acid from 9Z-retinoids or from Z- or di-Z-carotenoids. In addition, excessive residual unutilized mother liquor(s) have to be discarded.

A further weak point of all existing processes is that the composition of the mother liquors which are used is poorly characterized, and large volumes have to be moved in order to utilize the (2Z,4E)-C15-triarylphosphonium salt present therein in a few percent in suitable form.

With the specialist knowledge existing to date, however, still no solution has been found to overcome these difficulties which have already existed for many years.

In view of this shortcoming, it is an object of the invention to eliminate the disadvantages of the prior art and to provide a process with which an olefinically unsaturated phosphonium salt having at least two olefinic double bonds is obtained in high yields compared to the prior art, the phosphonium salt having Z configuration with respect to one olefinic double bond and E configuration with respect to at least one further olefinic double bond. In particular, the aim is to provide a C15-triarylphosphonium salt in which one olefinic double bond has Z configuration and at least one further olefinic double bond is present in an E conformation, especially one having the structural formula or general formula 1. The process is to be simple and rapid in its performance and applicable to industrial scale plants without difficulties, but at the same time inexpensive and energy-efficient, and should produce a minimum level of by-products, if possible none at all. Any by-products which occur should be of such a nature that the disposal or landfill dumping thereof is avoidable. It is a further object of the invention to indicate suitable uses for the compounds prepared by the process according to the invention.

This object is achieved in an impressively simple manner by a process for preparing [(2Z,4E)-3-methyl-5-(2,6,6-trimethylcyclohexen-1-yl)penta-2,4-dienyl]triphenylphosphonium salt of the general formula (1)

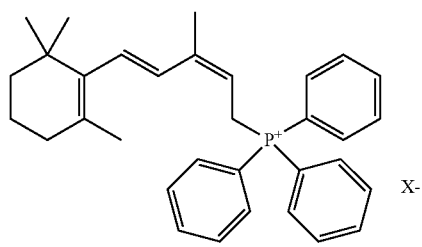

1 by isomerizing [(2E,4E)-3-methyl-5-(2,6,6-trimethylcyclohexen-1-yl)penta-2,4-dienyl]-triphenylphosphonium salt of the general formula (2),

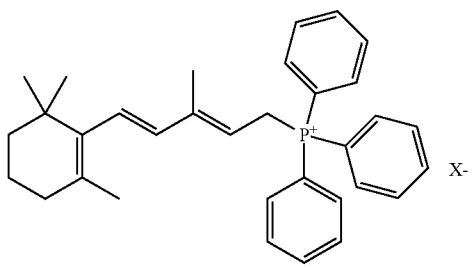

2 where the molar mass of the anion $X^-$ is not more than 200 g/mol.

This process—in contrast to those very complex and costly prior art processes—no longer makes use of the mother liquors which are used continually therein and which have a low concentration of compound of the general formula 1, occupy a large volume and additionally comprise a mixed fraction which, as already mentioned, has been little characterized. Instead, the reactant used is a (2E,4E)-C15-triarylphosphonium salt, especially that of the general formula or structural formula 2. By virtue of this process, the crystals obtained from the reaction mixture of the phosphonium salt synthesis, especially those of the general formula 2, are for the first time also usable directly for the preparation of compounds of the general formula 1, combined with a considerable rise in the yield of compound 1. This is because the amount of compound 1 available for a subsequent Wittig reaction now does not result solely from the proportion which is obtained from the mother liquor, but from the sum of the proportion from the mother liquor plus that proportion of compound of the general formula 1 which is obtained by the process according to the invention.

The person skilled in the art would not have expected that compounds of the general formula 2 can be isomerized to those of the general formula 1, since reactions of unsaturated phosphonium salts shown on the next page generally occur especially at temperatures above 50° C.

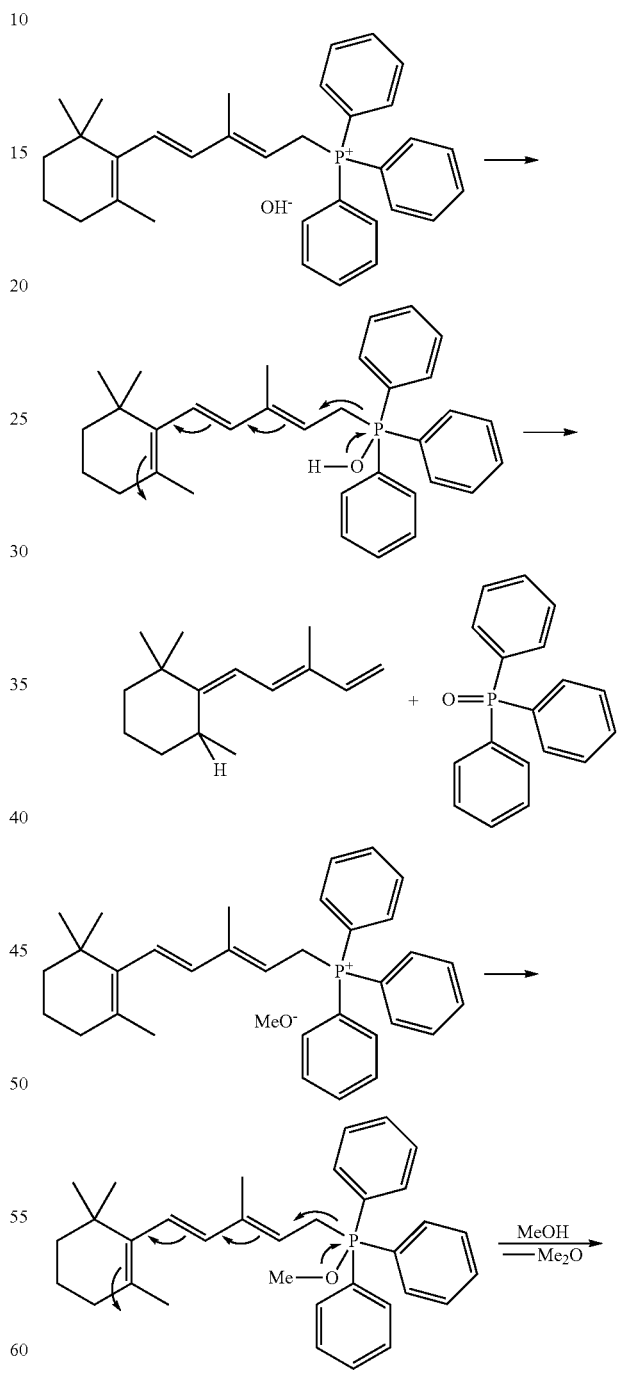

-continued

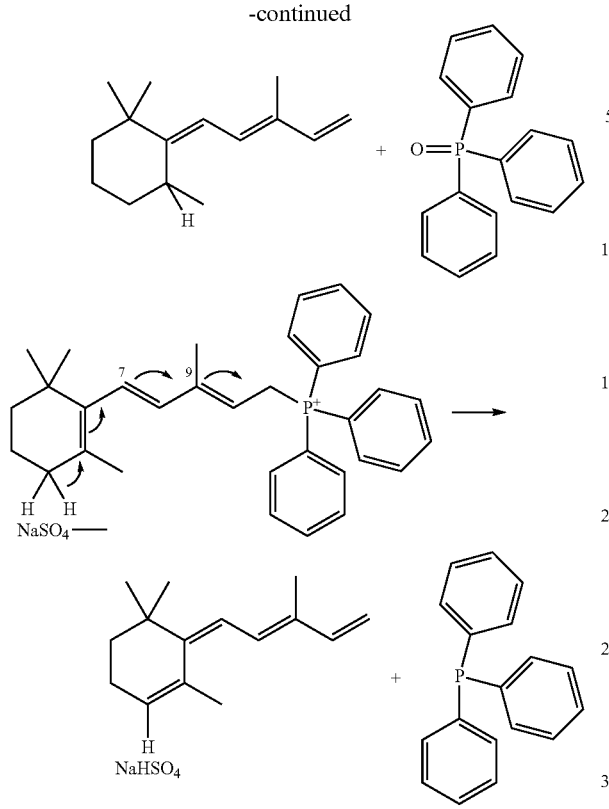

It can be seen that, in the presence of various nucleophiles or in the presence of sodium sulfate, a proton is eliminated or moved and triphenylphosphine oxide is subsequently released. The compounds of the general formula 2 used in accordance with the invention should not be any exception here and should react in the manner shown on the previous page.

Experimentally, however, something different has been found, namely the unexpected maintenance of the empirical formula and the isomerization of a (2E,4E)-C15-triarylphosphonium salt to a (2Z,4E)-C15-triarylphosphonium salt. Even at temperatures of 130° C., 145° C. and even at 180° C., there is no expected decomposition of the unsaturated phosphonium salts.

If the aim is to obtain a very substantially pure and additionally high proportion of compound of the general formula 1, a further configuration of the invention envisages preparing the [(2Z,4E)-3-methyl-5-(2,6,6-trimethylcyclohexen-1-yl)penta-2,4-dienyl]triphenylphosphonium salt of the general formula 1

1

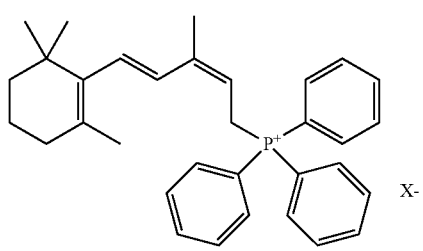

in accordance with the process by isomerizing the pure, well-characterized solid [(2E,4E)-3-methyl-5-(2,6,6-trimethylcyclohexen-1-yl)penta-2,4-dienyl]triphenylphosphonium salt of the general formula 2

2

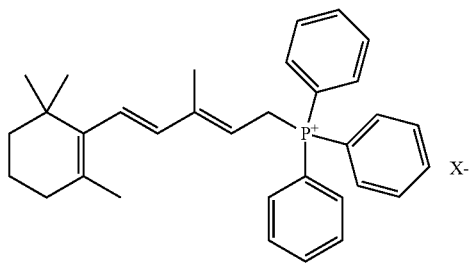

where the molar mass of the anion X– is not more than 200 g/mol.

The term "pure, well-characterized solid" in the context of the invention is understood exclusively to mean a form of compounds of the general formula 2 purified by crystallization or other purification processes and, in a particularly preferred embodiment, a crystalline form of compounds of the general formula 2.

In another embodiment, the aim of which is high yields of compound of the general formula 1, the process according to the invention envisages preparing [(2Z,4E)-3-methyl-5-(2,6,6-trimethylcyclohexen-1-yl)penta-2,4-dienyl]triphenylphosphonium salt of the general formula 1

1

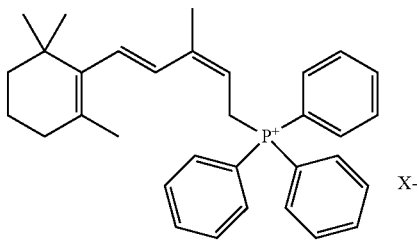

by isomerizing [(2E,4E)-3-methyl-5-(2,6,6-trimethylcyclohexen-1-yl)penta-2,4-dienyl]triphenylphosphonium salt of the general formula 2

2

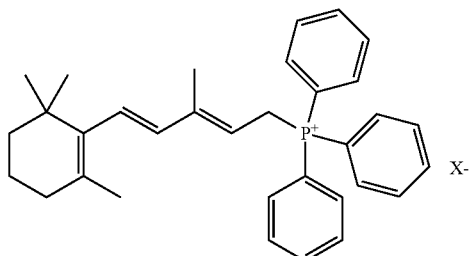

where the molar mass of the anion X– is not more than 200 g/mol, and obtaining the compound of the general formula 2 by crystallization from the reaction mixture of the reaction for preparation of this compound 2, and additionally by crystallization from a reaction mixture which arises according to the inventive process regime, i.e. isomerization.

In this embodiment, in which the compound of the general formula 2 is not completely isomerized by the process according to the invention, unreacted compound of the general formula 2 is combined again with newly used compound of the general formula 2 (obtained by crystallization and/or directly from the mother liquor of the reaction for preparation of compounds 2) and the overall yield of compound of the general formula 1 is thus increased, combined with a reduction in the proportion of unconverted compound of the general formula 2. This method of recycling unconverted compound of the general formula 2 can be performed continuously, i.e. in a circulation process, or else discontinuously.

According to the invention, "continuously" or "in a circulation process" mean pumping the reaction solution or the reaction mixture continually through a heated tube, constantly withdrawing reaction mixture at a point beyond the heated tube and constantly supplying compound of the general formula 2 at another point upstream of the heated tube.

"Discontinuously" in the context of this disclosure means filling the reaction vessel or the reactor, conducting the inventive reaction, cooling the reaction mixture, emptying the reactor or the reaction vessel and starting again from the outset.

The term "olefinic double bond" in the context of this invention comprises any double bond between two carbon atoms which is not part of an aromatic or cyclic carbon ring or other carbon heterocycle.

The term "olefinically unsaturated phosphonium salt having at least two olefinic double bonds" is understood to mean any phosphonium salt comprising at least two carbon-carbon double bonds which cannot be assigned to an aromatic or cyclic carbon ring system or carbon heterocycle.

A "C15-triarylphosphonium salt" in the context of this disclosure is an olefinically unsaturated phosphonium salt which bears three aromatic radicals and one carbon radical composed of 15 carbon atoms on the phosphorus atom. This carbon radical composed of 15 carbon atoms comprises at least two olefinic double bonds each in any conformation.

In a "(2E,4E)-C15-triarylphosphonium salt", the double bond at position 2 in the carbon radical composed of 15 carbon atoms, viewed from the phosphorus, has E conformation, and that at position 4 likewise has such an E conformation.

A "(2Z,4E)-C15-triarylphosphonium salt" differs from the corresponding 2E,4E isomer by a Z-configured double bond at position 2, viewed from the phosphorus.

The process according to the invention is applicable to a multitude of olefinically unsaturated phosphonium salts having at least two olefinic double bonds. For instance, it is possible to use all those salts of this kind wherein the anion X− is selected from the group consisting of halide, dihydrogenphosphate, hydrogenphosphate, phosphate, nitrate, hydrogensulfate, sulfate, chlorate, perchlorate, tetrafluoroborate, C1-C4-alkanoates, especially acetate, C1-C7-sulfonates, especially methanesulfonate, benzenesulfonate and toluenesulfonate. Therefore, no limits are placed on the process according to the invention by the nature of the counterion X− or anion X−.

By means of time-consuming experiments, it was found that good yields and appropriate reaction times are achieved when X− is selected from the group consisting of fluoride, chloride, bromide, iodide, sulfate, hydrogensulfate, methanesulfonate, benzenesulfonate and toluenesulfonate.

Inventive C1-C4-alkanoates comprise formate, acetate, propionate, butyrate, isobutyrate, i.e anions of the corresponding carboxylic acid. C1-C7-Sulfonates in the context of the invention comprise methanesulfonate, synonymous with mesylate, trifluoromethanesulfonate, synonymous with triflate, benzenesulfonate and toluenesulfonate.

In an inexpensive execution of the inventive process, the isomerization is a thermal isomerization. Specifically on the industrial scale, this configuration is important since, in a continuous and even more so in a discontinuous process regime, heating or cooling of the reaction mixture is much easier to accomplish than selectively mounting light sources needed for a photo isomerization, and switching them on and off. These are usually UV lights which are expensive to procure and are prone to faults specifically when switched on and off frequently.

The isomerization according to the invention takes place at elevated temperature. In general, the olefinically unsaturated phosphonium salts having at least two olefinic double bonds are isomerized within a temperature range from 50° C. to 200° C., preferably from 100° C. to 180° C. and more preferably within a temperature range from 120° C. to 180° C. A particularly preferred temperature range for the isomerization is that from 130° C. to 180° C. When working within the temperature window employed, viable yields are obtained with non-excessive energy consumption. This is also the case specifically when unreacted compound of the general formula 2 is fed back to the isomerization process according to the invention. This is especially true of an execution in which, in accordance with the invention, [(2Z,4E)-3-methyl-5-(2,6,6-trimethylcyclohexen-1-yl)penta-2,4-dienyl]triphenylphosphonium hydrogensulfate is prepared by thermal isomerization by reacting the [(2E,4E)-3-methyl-5-(2,6,6-trimethylcyclohexen-1-yl)penta-2,4-dienyl] triphenylphosphonium hydrogensulfate within a temperature range from 50 to 200° C., preferably from 100° C. to 180° C. and more preferably within a range from 120 to 180° C. For this latter embodiment too, particular preference is also given to working within a temperature range from 130° C. to 180° C.

Due to the increasing oxidation sensitivity of the C15-triarylphosphonium salts and especially of the compounds used in claim 1, which is observed especially at temperatures of 50° C. or higher, the process according to the invention is performed under inert gas, and for reasons of cost preferably under nitrogen or argon.

"Inert gas" in the context of the invention is understood to mean any gas or gas mixture which is slow to react and is selected from at least one of the compounds neon, argon, krypton and nitrogen.

In a further configuration of the inventive process, the isomerization is performed within a pressure range from 1 to 100 bar, preferably from 5 to 80 bar, more preferably within a pressure range from 8 to 50 bar and most preferably within a pressure range from 10 to 25 bar. Working under elevated pressure allows operation of the isomerization reaction according to the invention at comparatively low temperatures. This reduces the thermal stress for the compounds used and has a yield-enhancing effect. If low-boiling solvents are used, it is advantageous and sometimes unavoidable to work under elevated pressure, in order not to convert the solvent partly or completely to the vapor phase during the reaction and thus both to prolong the reaction time and to reduce the yield of (2Z,4E)-C15-triarylphosphonium salt.

In a variant which affords high yields within a short time, the inventive process is performed within a temperature range from 50° C. to 200° C. and at a pressure of 1 to 100 bar, preferably within a temperature range from 100° C. to 180° C. and at a pressure of 8 to 50 bar and most preferably within a temperature range from 120° C. to 180° C. and at a pressure of 10 to 25 bar.

The subject of a further modification of the invention is to perform the isomerization in a solvent or a solvent mixture. Many of the olefinically unsaturated phosphonium salts having at least two olefinic double bonds in the E conformation, especially most of the (2E,4E)-C15-triarylphosphonium salts, cannot be converted to a liquid form in substance and reacted by the process according to the invention. Equally, it is impossible to subject them to said process in solid form, since they would at least partly decompose. Therefore, such entities can be converted by the process only in a solvent.

For the reasons mentioned above, the isomerization according to the invention is preferably performed in such a way that the C15-triarylphosphonium salt of the general formula 2 is dissolved or suspended in a suitable solvent and heated. In order to achieve very rapid reaction combined with very brief thermal stress on the compound in question, isomerization in the dissolved state is the preferred mode of operation.

Solvents or solvent mixtures particularly suitable for the process according to the invention are those which are selected from the group consisting of toluene, xylene, dioxane, THF, DMF, DMSO, C1-C6-alcohol, C3-C7-ketone, ethyl acetate, propyl acetate, butyl acetate, ethyl propionate, or from a mixture of at least two of these compounds. They can be separated by means of different processes, but nevertheless easily, again from the product obtained by the process, and ensure that as good as no by-products are obtained, or else the by-product spectrum is quite narrow. It has been found to be particularly effective in this regard to select the solvent or solvent mixture from the group consisting of methanol, ethyl acetate, propyl acetate, or from a mixture of at least two of these compounds.

C1-C6-Alcohol is understood in the context of the invention to mean all alcohols comprising at least one and at most six carbon atom(s). Primary, secondary and tertiary alcohols are all encompassed, preference being given to the primary alcohols over the secondary and preference being given in turn to the latter over the tertiary alcohols. Effectively, the C1-C6-alcohols include monohydric, dihydric and trihydric alcohols. Here too, the monohydric alcohols have been found to have better suitability than the dihydric alcohols, and these in turn to have better suitability than the trihydric alcohols. C1-C6-Alcohols comprise, according to the invention, at least one representative selected from the group consisting of methanol, ethanol, 2-methoxyethanol, n-propanol, isopropanol, 2-methoxy-1-propanol, n-butanol, isobutanol or isobutyl alcohol or sec-butyl alcohol, tert-butanol or tert-butyl alcohol, n-pentanol, 2-pentanol, isopentyl alcohol, isoamyl alcohol or 3-pentanol, 2-methyl-1-butanol, neopentyl alcohol, tert-pentyl alcohol, n-hexanol, 1,3-dimethylbutanol or amylmethyl alcohol, diacetone alcohol, methylisobutylcarbinol, tert-hexyl alcohol, cyclohexanol, ethylene glycol, propylene glycol, 1,2-propanediol, 1,3-propanediol, 1,2-butanediol, 1,3-butanediol, 1,4-butanediol, 2,3-butanediol, diethylene glycol, 2-methyl-2,3-butanediol, 1,5-pentanediol, 1,4-pentanediol, 1,3-pentanediol, 1,2-pentanediol, 2,4-pentanediol, neopentyl glycol, 1,6-hexanediol, 1,5-hexanediol, 1,4-hexanediol, 1,3-hexanediol, 2-methyl-2,4-pentanediol, pinacol or 2,3-dimethyl-2,3-butanediol, glycerol, 1,2,3-butanetriol, 1,2,4-butanetriol, 1,2,5-hexanetriol, 1,2,6-hexanetriol, trimethylolpropane.

C3-C7-Ketones in the context of this disclosure comprise at least one compound selected from the group consisting of acetone, methyl ethyl ketone or butanone, methyl n-propyl ketone, methyl isopropyl ketone, diethyl ketone, gamma-butyrolactone, methyl n-butyl ketone, methyl isobutyl ketone, methyl-2-pyrrolidone, di-n-propyl ketone, diisopropyl ketone, cyclohexanone, ethyl n-butyl ketone, diacetone alcohol, acetonylacetone, methyl n-amyl ketone or 2-heptanone, methyl isoamyl ketone, methylcyclohexanone. In the same way, mixtures of two or more of the aforementioned compounds can also be covered by the term C3-C7-ketones.

For reasons of cost, and additionally because it can be separated easily from the reaction mixture, the process according to the invention, in a particularly preferred execution, envisages using methanol as the solvent.

This execution is additionally improved by the fact that the inventive isomerization is performed in methanol as a solvent at 10 to 30 bar, preferably at 13 to 20 bar and more preferably at 13 to 16 bar. This measure profits not just from an inexpensive solvent which is easy to remove again, but also counteracts any formation of by-products or degradation products since the reaction regime under pressure can work at correspondingly lower temperatures. As a result, local heating and therefore said by-products or degradation products occur only in even smaller amounts.

A further optimization of the inventive process for preparing [(2Z,4E)-3-methyl-5-(2,6,6-trimethylcyclohexen-1-yl)penta-2,4-dienyl]triphenylphosphonium salt of the general formula 1

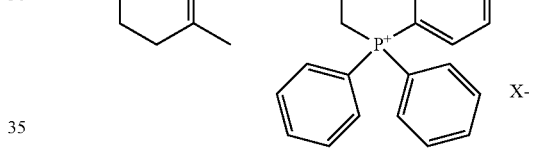

is possible by isomerization of [(2E,4E)-3-methyl-5-(2,6,6-trimethylcyclohexen-1-yl)penta-2,4-dienyl]triphenylphosphonium salt of the general formula 2,

2 in methanol within a temperature range from 50° C. to 200° C. and at a pressure of 1 to 100 bar, preferably within a temperature range from 100° C. to 180° C. and at a pressure of 8 to 50 bar, and most preferably within a temperature range from 120° C. to 180° C. and at a pressure of 10 to 25 bar, where the molar mass of the anion X− is not more than 200 g/mol.

Particular olefinically unsaturated phosphonium salts having at least two olefinic double bonds each in the E conformation can be converted only in a very time-consuming manner and very gradually by the process according to claim 1. This is the case for compounds including those olefinically unsaturated phosphonium salts which have two olefinic double bonds in the E conformation and which have a hydrogensulfate as the counterion. However, for these compounds too, especially for [(2E,4E)-3-methyl-5-(2,6,6-trimethylcyclohexen-1-yl)penta-2,4-dienyl]triphenylphosphonium hydrogensulfate, it is possible in an entirely unexpected manner, and unforeseeably to the person skilled in the art, to achieve high yields within a reasonable period by the process according to the invention when the isomerization is performed in the presence of a base.

An optimum for the reaction rate was achieved when, for the isomerization by the process, the base is added in such an amount that the anions formed therefrom are 0.1 to 1 molar equivalent based on compound 2, preferably 0.2 to 0.7 molar equivalent and more preferably 0.25 to 0.5 molar equivalent. A molar equivalent is understood to mean that molar amount of anions formed which correspond to the molar amount of compound 2. In this reaction, the sulfate of the base used is generally obtained in solid form.

Bases in the sense of the process disclosed are:

At least one organic base selected from the group consisting of 1-amino-2-propanol, amino-guanidines, arginine, benzylamines, benzyldimethylamine, N,N'-bis(2-aminoethyl)-1,2-diaminoethane, bis(2-aminoethyl)amines, bis(2-fluoro-2,2-dinitroethyl)amine, 1,2-bis(dimethylamino)-ethane, butylamines, 2-butylamines, butylethylamines, calcium methoxide, cyclohexylamines, cyclopentylamines, di-2-butylamines, 1,4-diaminobenzene, 1,2-diaminoethane, 1,2-diaminopropane, 1,3-diaminopropane, 1,4-diazabicyclo[2.2.2]octane, dibutylamine, 3-dibutylamino-propylamine, diethylamine, 3-diethylaminopropylamine, diethylenetriamine, diisobutylamine, diisopropylamine, 3,3'-dimethoxy-4,4'-diaminobiphenyl, dimethylamine, 2-dimethylaminoethylamine, N,N-dimethylaniline and derivatives thereof, 1,3-dimethylbutylamine, 2,6-dimethyl-piperidine and derivatives thereof, 2,2-dimethylpropylamine, 1,2-dimethylpropylamine, 1,1-dimethylpropylamine, N,N-dimethylpropylamine, dipropylamine, 5-ethyl-2-methylpyridine, ethylamine, ethyldimethylamine, ethylenediamine, 1-ethylpiperidine, 2-ethylpiperidine, urea, hexamethylenetetramine, histidine, N-2-hydroxyethyl-1,2-diaminoethane, 2-hydroxyethylamine, sodium methoxide, sodium ethoxide, sodium isopropoxide, N-2-hydroxyethyldimethylamine, isobutylamine, isopentylamine, isopropylamine, potassium methoxide, potassium ethoxide, potassium propoxide, potassium isopropoxide, lithiumdiisopropylamide, lithium methoxide, lithium ethoxide, lithium propoxide, lithium isopropoxide, lysine, magnesium methoxide, melamine, methylamine, N-methylbutylamine, 4-methylmorpholine, 1-methylpiperidine, 2-methylpiperidine, 3-methylpiperidine, 4-methylpiperidine, 2-methylpyridine, N-methyl-pyrrolidine, morpholine and derivatives thereof, pentylamine, N-phenylhydroxylamine, piperazine and derivatives thereof, piperidine and derivatives thereof, propylamine, pyridine and derivatives thereof, quinoline and derivatives thereof, 1,2,3,6-tetrahydropyridine and derivatives thereof, 1,3,4,7-tetramethylisoindole, 1,2,4,5-tetrazine, thiourea, 3,6,9-triaza-11-amino-undecanol, 1,3,5-triazine, triethylamine, trimethylamine, 2,4,6-tris(dimethylaminomethyl)phenol, tris(hydroxymethyl)methylamine, vinylpyridines or mixtures of these compounds.

Bases in the context of the process disclosed are additionally:

At least one inorganic base selected from the group consisting of ammonia, ammonium hydroxide, barium hydroxide, barium oxide, lead carbonate, lead hydroxide, cesium amide, calcium carbonate, calcium hydroxide, calcium oxide, potassium carbonate, potassium hydroxide, lithium carbonate, lithium hydroxide, dilithium oxide, magnesium carbonate, magnesium hydroxide, magnesium oxide, sodium carbonate, sodium hydroxide, disodium oxide, silver oxide, strontium hydroxide, strontium oxide or mixtures thereof.

In a developed variant, the inventive process is performed in the presence of a base selected from at least one organic base and at least one inorganic base.

It has been found to be advantageous for process economy to use those bases which form the solvent as they react. Thus, in a preferred process variant, the isomerization is performed in the presence of a base selected from the group consisting of sodium methoxide, potassium methoxide, magnesium methoxide, calcium methoxide, lithium methoxide.

In a very preferred configuration of the process according to the invention, (2Z,4E)-3-methyl-5-(2,6,6-trimethylcyclohexen-1-yl)penta-2,4-dienyl]triphenylphosphonium salt of the general formula 1

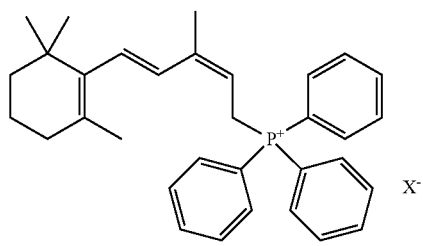

1 is prepared by isomerizing [(2E,4E)-3-methyl-5-(2,6,6-trimethylcyclohexen-1-yl)penta-2,4-dienyl]triphenyl phosphorium hydrogensulfate of the formula 2'

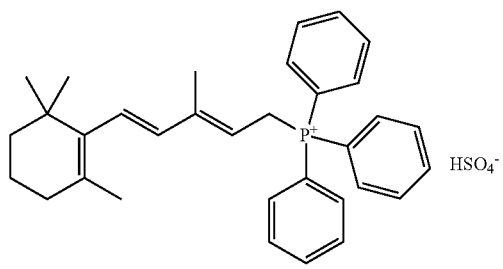

2' where the molar mass of the anion X– is not more than 200 g/mol, by performing the isomerization in the presence of a base selected from the group consisting of sodium methoxide, potassium methoxide, magnesium methoxide, calcium methoxide, lithium methoxide.

It has been examined whether the time at which base is added has an influence on reaction rate and yield. In fact, both were positively influenced when, in a further advancement of the inventive process, the isomerization is performed in the presence of a base and the latter is added at an early stage, prior to commencement of the isomerization.

In a specialized development of the process according to the invention, (2Z,4E)-3-methyl-5-(2,6,6-trimethylcyclohexen-1-yl)penta-2,4-dienyl]triphenylphosphonium salt of the general formula 1

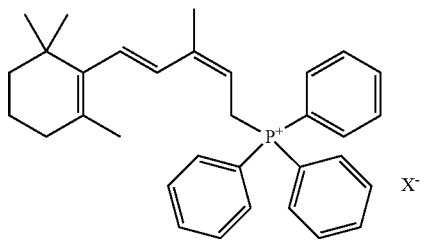

is prepared by isomerizing [(2E,4E)-3-methyl-5-(2,6,6-trimethylcyclohexen-1-yl)penta-2,4-dienyl]triphenyl phosphorium hydrogensulfate of the formula 2'

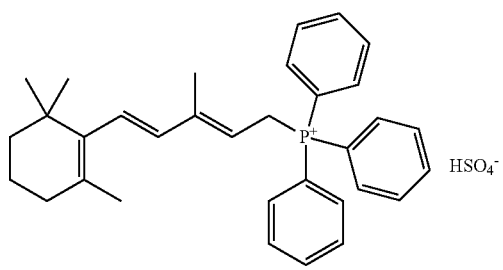

where the molar mass of the anion X– is not more than 200 g/mol,
by performing the isomerization in the presence of a base and adding the latter at an early stage, prior to commencement of the isomerization.

It is particularly resource-friendly when the base for the aforementioned embodiment of the process is selected from the group consisting of sodium methoxide, potassium methoxide, magnesium methoxide, calcium methoxide, lithium methoxide.

Since the olefinically unsaturated phosphonium salts having at least two olefinic double bonds are not of unlimited stability under the isomerization conditions, it is advantageous to select the reactor design such that it is based on a fixed mode of operation, especially an isothermal mode of operation, and the reaction mixture is exposed to the reaction conditions for an exactly defined residence time. Only then can premature degradation of said salts or the occurrence of side reactions be avoided or at least reduced in degree. Therefore, the invention, in a further configuration, envisages performing the isomerization in a reactor with a fixed temperature profile, especially with an isothermal temperature profile, and an exactly fixed residence time.

"Fixed temperature profile" in the light of this disclosure is to mean exactly fixing the temperature on commencement of the inventive isomerization, the heating rate, the intermediate temperatures, the temperature ramps and the periods of constant temperature, as well as the end temperature of the inventive isomerization process. This exact fixing has a yield-enhancing and reaction-accelerating effect.

"Isothermal temperature profile" in the sense of the process according to the invention means leaving the compound of the general formula 2 at a particular temperature over the entire reaction time required for the isomerization, the exactly fixed residence time. This temperature is a value selected from the already above-specified temperature ranges from 50° C. to 200° C., preferably from 100° C. to 180° C., further preferably from 120° C. to 180° C. and more preferably from 130° C. to 180° C. It has been found that these temperatures, as a consequence of the preference therefor, have a positive effect both with regard to brevity of the reaction time and relation to the yield and by-product spectrum.

The term "exactly fixed residence time" according to the invention is understood to mean the time span or duration over which the compound of the general formula 2 is exposed to the particular temperature or the fixed temperature profile, i.e. is within the isothermal temperature profile.

In a further advancement of the inventive process which optimizes yield and reaction time further, the isomerization is performed in a reactor with a fixed temperature profile, especially with an isothermal temperature profile, and an exactly fixed residence time which is a selected value within a time span from 5 to 35 min, preferably from 5 to 25 min and, in a particularly preferred variant, from 10 to 25 min.

A developed process which takes into account the above statements therefore envisages preparing [(2Z,4E)-3-methyl-5-(2,6,6-trimethylcyclohexen-1-yl)penta-2,4-dienyl]triphenylphosphonium salt of the general formula 1

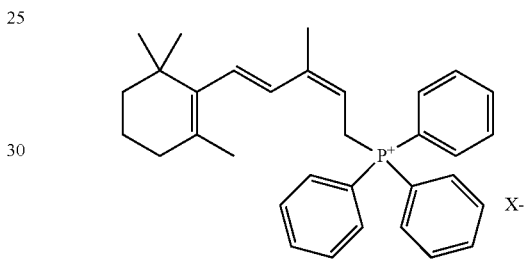

by isomerizing [(2E,4E)-3-methyl-5-(2,6,6-trimethylcyclohexen-1-yl)penta-2,4-dienyl]triphenylphosphonium salt of the general formula 2,

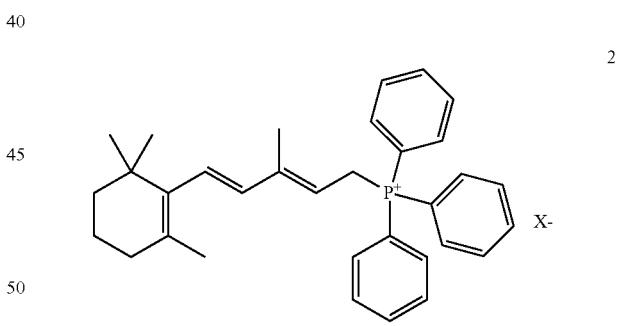

where the molar mass of the anion X– is not more than 200 g/mol,
by performing the isomerization in a reactor with an isothermal temperature profile at a temperature of 120° C. to 180° C., preferably from 130° C. to 160° C., and with an exactly fixed residence time which is a selected value within a time span from 10 to 25 min, preferably within a time span from 15 to 25 min.

This developed process has been found to be particularly suitable for the conversion of a compound of the general formula 2 in which the anion X– is hydrogensulfate. It can be operated in a particularly time-saving manner with hydrogensulfate as the anion X– when the isomerization is performed in the presence of a base.

In another execution of the process according to the invention for preparing [(2Z,4E)-3-methyl-5-(2,6,6-trimethylcyclohexen-1-yl)penta-2,4-dienyl]triphenylphosphonium salt of the general formula 1

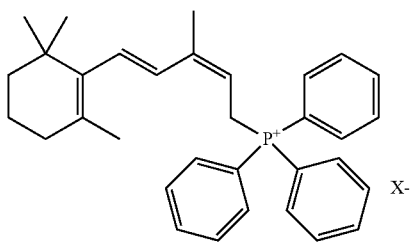

1 by isomerizing [(2E,4E)-3-methyl-5-(2,6,6-trimethylcyclohexen-1-yl)penta-2,4-dienyl]triphenylphosphonium salt of the general formula 2

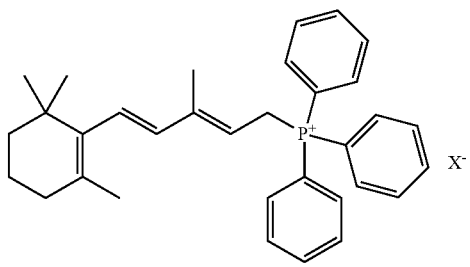

2 where the molar mass of the anion X– is not more than 200 g/mol,
the isomerization is performed in a reactor having an isothermal temperature profile at a temperature of 120° C. to 180° C., preferably from 130° C. to 170° C., with an exactly fixed residence time which is a selected value within a time span from 5 to 15 min, preferably within a time span from 10 to 15 min.

This execution of the inventive process is particularly suitable for a compound of the general formula 2 in which the anion X– is chloride. Particularly good yields of [(2Z,4E)-3-methyl-5-(2,6,6-trimethylcyclohexen-1-yl)penta-2,4-dienyl] triphenylphosphonium salt of the general formula 1 are achieved with an exactly fixed residence time of 10 min.

A further variant of the inventive process envisages preparing [(2Z,4E)-3-methyl-5-(2,6,6-trimethylcyclohexen-1-yl)penta-2,4-dienyl]triphenylphosphonium salt of the general formula 1

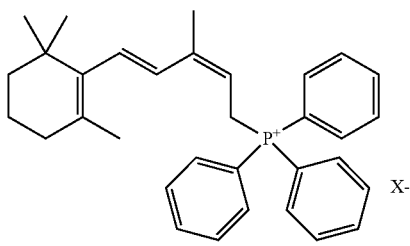

1 by isomerizing [(2E,4E)-3-methyl-5-(2,6,6-trimethylcyclohexen-1-yl)penta-2,4-dienyl]triphenylphosphonium salt of the general formula 2,

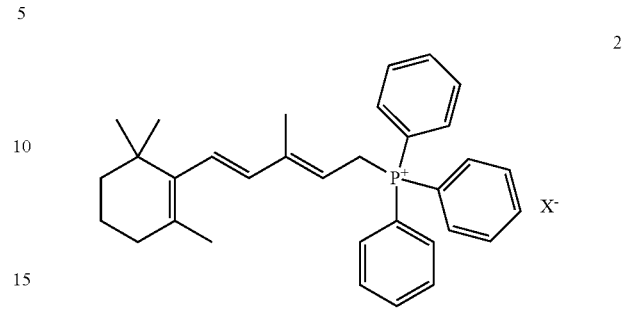

2 where the molar mass of the anion X– is not more than 200 g/mol,
by performing the isomerization in a reactor with an isothermal temperature profile at a temperature of 150° C. to 190° C., preferably of 160° C. to 180° C., and an exactly fixed residence time which is a selected value within a time span of 5 to 15 min, preferably within a time span of 10 to 15 min.

It is a feature of this variant of the inventive process that it gives good yields in a timely manner particularly when the anion X– of the compound of the general formula 2 is a tosylate anion.

For the inventive process, it is advantageous in relation to yield, reduced by-product spectrum and reaction rate when a fixed temperature profile is employed, especially an isothermal temperature profile and an exactly fixed residence time. At the same time, rapid and homogeneous mixing of the reactants or of the reaction mixture also contributes thereto. These requirements are satisfied in an impressive manner when, in a continuation of the invention, the reactor used is a microwave reactor or a flow tube reactor.

A flow tube reactor in the context of the invention is a vessel with an inlet and an outlet, through which reaction mixture is pumped continuously or discontinuously. The pumping rate is adjustable such that the reaction mixture resides for the exactly fixed residence time in the flow reactor. During this residence time, the flow tube reactor is heated such that the fixed temperature profile, the particular temperature or the claimed temperature range is distributed constantly over the volume of the flow tube reactor. Therefore, the reaction mixture experiences yield-enhancing homogeneous heat treatment along the flow tube reactor, and this is attainable more rapidly through actuation of a stirrer apparatus present in said reactor, especially on commencement of the inventive reaction.

An inventive microwave reactor is a vessel in which the reaction mixture is heated by means of microwaves to the fixed temperature profile, to the particular temperature or to the claimed temperature range. Heating by microwaves gives the advantage that the heat is distributed very homogeneously. Because the heating takes place from the inside of the reaction space outward, homogeneous mixing, stirrer-driven under some circumstances, of the reaction mixture is possible much more easily than in the case of a conventional heat source.

In cases in which the isomerization by the process according to the invention leads to a mixture of the olefinically unsaturated phosphonium salts having at least two olefinic double bonds, especially of the compounds of the general formula 1 and those of the general formula 2, it is necessary to separate these compounds from one another. Therefore, a continuation of said process involves, after the isomerization, removing unreacted compounds of the general formula 2 in solid form and isolating the filtrate obtained. Further processing is possible directly in successive reaction steps.

An enhanced yield is also achieved by the extension of the process according to the invention of removing and recycling any unreacted starting material of the general formula 2 after the isomerization.

"After the isomerization" means the time at which the reaction mixture is conducted out of a reaction vessel or the reactor in which it was present with the fixed temperature profile, especially with the isothermal temperature profile, or at the particular temperature or within the claimed temperature range, for an exactly fixed residence time.

The starting material is the olefinically unsaturated phosphonium salt having at least two olefinically unsaturated double bonds, especially the C15-triarylphosphonium salt and very particularly the (2E,4E)-C15-triarylphosphonium salt of the general formula 2 in the presence of the solvent, or else in solvent-free form. The exocyclic double bonds of all or of the predominant fraction of the compounds covered by the starting material have an all-E or all-trans conformation.

The term "removal" of any unreacted starting material is understood to mean any removal of said starting material from the reaction mixture. This includes the methods of extraction and any kind of chromatographic separation methods.

It has been found that the starting material, especially the compounds of the general formula 2, can be separated out of a solution as solids, whereas those olefinically unsaturated phosphonium salts having at least two olefinic double bonds, one of which has Z and another E conformation, especially those C15-triarylphosphonium salts having such a conformation and very particularly the compounds of the general formula 1, remain in solution. Therefore, the inventive process, in an inexpensive and time-saving development, envisages removing any unreacted starting material of the general formula 2 by crystallization and recycling it after the isomerization.

Some olefinically unsaturated phosphonium salts having at least two olefinic double bonds, both of which have E conformation, especially some C15-triarylphosphonium salts of this type and in particular some (2E,4E)-C15-triarylphosphonium salts of the general formula 2, cannot only not be converted completely to the corresponding phosphonium salt having at least two olefinic double bonds, of which one has Z and another E conformation, but also do not precipitate directly out of the reaction mixture after the end of the isomerization. This problem is taken into account by the inventive process in one configuration by freeing any unreacted starting material of the general formula 2 from the solvent after the isomerization, taking it up in a solvent or solvent mixture which promotes the crystallization of the [(2E,4E)-3-methyl-5-(2,6,6-trimethylcyclohexen-1-yl)penta-2,4-dienyl]triphenylphosphonium salt, preferably in a branched alcohol and more preferably isopropanol, removing it by crystallization and recycling it.

The term "recycled" according to the invention should be interpreted broadly. It means that, in a separate setup or an isolated apparatus, starting material removed from the reaction mixture is fed back to the isomerization. It likewise means, however, conducting the process according to the invention in circulation, removing the remaining starting material at a point in the circuit, and feeding it back to the circuit at another point.

The starting material preferably removed by crystallization can be recycled again in solid form. It has been found, however, that this leads to poorer mixing and to inhomogeneity in the reaction mixture, combined with yield losses. Therefore, a developed execution of the process according to the invention envisages removing any unreacted starting material of the general formula 2 by crystallization after the isomerization, redissolving the solids obtained in the solvent or in the solvent mixture of isomerization, and recycling it. More particularly, this developed execution envisages freeing any unreacted starting material of the general formula 2 of the solvent after the isomerization, taking it up in a solvent or solvent mixture which promotes the crystallization of the [(2E,4E)-3-methyl-5-(2,6,6-trimethylcyclohexen-1-yl) penta-2,4-dienyl]triphenylphosphonium salt, preferably in a branched alcohol and more preferably isopropanol, removing it by crystallization, redissolving the solid obtained in the solvent or in the solvent mixture of isomerization, and recycling it.

Solvents or solvent mixtures which promote the crystallization of the [(2E,4E)-3-methyl-5-(2,6,6-trimethylcyclohexen-1-yl)penta-2,4-dienyl]-triphenylphosphonium salt comprise, as well as isopropanol, also isopropanol to which small amounts of a hydrocarbon, preferably heptane, have been added.

Such a hydrocarbon is selected from the group consisting of hydrocarbons comprising at least 5 carbon atoms and at most 10 carbon atoms. More particularly, it is selected from the group comprising n-pentane, iso- and tert-pentane, each in all of the isomeric forms thereof, n-hexane and all hexane isomers, n-heptane and all isomers of heptane, n-octane and all octane isomers, n-nonane and all isomers of nonane, n-decane and all decane isomers, toluene, alkyl-substituted benzenes where alkyl comprises 1 to 5 carbon atoms, and from mixtures of at least two of the aforementioned individual compounds. These individual compounds include particularly a pentane, cyclopentane, methylcyclopentane, hexane, cyclohexane, heptane, methylcyclohexane, n-octane, 2-methylheptane, 3-methylheptane, 4-methylheptane, 2,2-dimethylhexane, 2,3-dimethylhexane, 2,4-dimethylhexane, 2,5-dimethylhexane, 3,3-dimethylhexane, 3,4-dimethylhexane, 3-ethylhexane, 2,2,3-trimethylpentane, 2,2,4-trimethylpentane (isooctane), 2,3,3-trimethylpentane, 2,3,4-trimethylpentane, 3-ethyl-2-methylpentane, 3-ethyl-3-methylpentane, 2,2,3,3-tetramethylbutane.

After the starting material has been removed as described above, what remains is generally a usually beige to brown oil or an oil of (2Z,4E)-C15-triarylphosphonium salt dissolved in the corresponding solvent, especially of the [(2Z,4E)-3-methyl-5-(2,6,6-trimethylcyclohexen-1-yl)-penta-2,4-dienyl] triphenylphosphonium salt of the general formula 1 having a purity of greater than 90%, preferably having a purity of greater than 95% and more preferably having a purity of greater than 98%, based on impurities still present.

In a particular development, the process according to the invention envisages exchanging the solvent present or the solvent mixture after the isomerization for an alcohol, preferably for a branched alcohol and more preferably for isopropanol, adding a hydrocarbon liquid at room temperature, cooling to a temperature in the range from −30° C. to 20° C., preferably to a temperature in the range from −30° C. to 10° C., incubating at this temperature and removing the solids obtained. This configuration of the inventive process is applicable to all olefinically unsaturated phosphonium salts having at least two olefinic double bonds used in the process. It is inexpensive and simple to perform and leads to very pure (2Z,4E)-C15-triarylphosphonium salts.

In another configuration, the inventive process requires that, after the isomerization in the presence of base, the solvent present or the solvent mixture be exchanged for an alcohol, preferably for a branched alcohol and more preferably for isopropanol, acidification be effected with an acid to a pH of 0 to 2, a hydrocarbon liquid at room temperature be added, the mixture be cooled to a temperature in the range from −30° C. to 20° C., preferably to a temperature in the range from −30° C. to 10° C., incubation be effected at this temperature and the solids obtained be removed.

This configuration of the inventive process is applicable to all olefinically unsaturated phosphonium salts having at least two olefinic double bonds used in the process; although it is not absolutely necessary, it has been found to be particularly useful with regard to yield and reaction time in the case of those olefinically unsaturated phosphonium salts which have at least two olefinic double bonds and have a hydrogensulfate as the anion X−, especially in the case of (2E,4E)-C15-triarylphosphonium hydrogensulfates and particularly in the case of [(2E,4E)-3-methyl-5-(2,6,6-trimethylcyclohexen-1-yl)penta-2,4-dienyl]triphenylphosphonium hydrogensulfate. It is also inexpensive and simple to perform and leads to very pure [(2Z,4E)-3-methyl-5-(2,6,6-trimethylcyclohexen-1-yl)penta-2,4-dienyl]triphenylphosphonium hydrogensulfate.

"Alcohols" or "branched alcohols" in the sense of the above-described process development are the alcohols or branched alcohols already mentioned above.

"Exchange" is supposed to mean, according to the invention, replacing the solvent or solvent mixture used completely with another solvent or solvent mixture.

The acid for use in accordance with the invention is selected from all acids with which a pH of 0 to 2 can be established. Particularly preferred representatives are selected from the group consisting of hydrochloric acid, nitric acid, sulfuric acid, perchloric acid, hydrobromic acid, hydriodic acid, hydrofluoric acid, phosphoric acid, chloric acid, trifluoroacetic acid, formic acid, sulfonic acids.

Hydrocarbons liquid at room temperature, in the context of the invention, are those already mentioned above and especially those selected from the group consisting of pentane, cyclopentane, methylcyclopentane, hexane, cyclohexane, heptane, methylcyclohexane, n-octane, 2-methylheptane, 3-methylheptane, 4-methylheptane, 2,2-dimethylhexane, 2,3-dimethylhexane, 2,4-dimethylhexane, 2,5-dimethylhexane, 3,3-dimethylhexane, 3,4-dimethylhexane, 3-ethylhexane, 2,2,3-trimethylpentane, 2,2,4-trimethylpentane (isooctane), 2,3,3-trimethylpentane, 2,3,4-trimethylpentane, 3-ethyl-2-methylpentane, 3-ethyl-3-methylpentane, 2,2,3,3-tetramethylbutane.

"Incubating" is understood to mean leaving the reaction mixture to rest at the given temperature for a period of 2 to 18 hours, preferably for a period of 4 to 15 hours and more preferably for a period of 8 to 12 hours.

In a variable procedure for workup of the reaction mixture after the isomerization, unreacted starting material of the general formula 2 is not removed therefrom, but instead concentration is effected directly to the product of the inventive process, namely the (2Z,4E)-C15-triarylphosphonium salt, especially the (2Z,4E)-C15-triarylphosphonium salt of the general formula 1.

This procedure extends the means of workup of the reaction mixture. It leads to the developed inventive process for preparing [(2Z,4E)-3-methyl-5-(2,6,6-trimethylcyclohexen-1-yl)penta-2,4-dienyl]triphenylphosphonium salt of the general formula 1

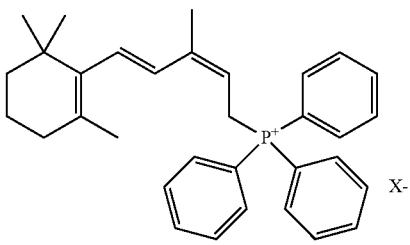

by isomerizing [(2E,4E)-3-methyl-5-(2,6,6-trimethylcyclohexen-1-yl)penta-2,4-dienyl]triphenylphosphonium salt of the general formula 2,

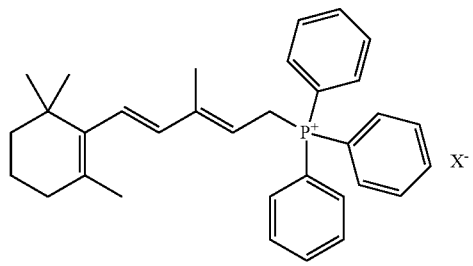

where the molar mass of the anion X− is not more than 200 g/mol,
and subsequently crystallizing the compound of the general formula 1 by adding seed crystals of this compound 1.

The invention further provides for the use of the compound 1 obtained by the process for preparation of 9Z-retinoids, and for preparation of carotenoids having at least one cis double bond.

9Z-Retinoids in the context of this disclosure comprise 9Z-retinol, 9Z-retinal, 9Z-retinoic acid, 9Z-retinoic acid alkali metal salts, 9Z-retinoic acid alkaline earth metal, 9Z-retinoic salts esters such as 9Z-retinoic acid fluorenylmethyl ester and 9Z-retinoic acid benzyl ester, and also lower alkyl esters of 9Z-retinoic acid where "lower alkyl" represents methyl, ethyl, n-propyl, isopropyl, n-butyl, isobutyl and tert-butyl. The cis or Z double bond at position 9 in these compounds relates to that double bond which is at position 2 and extends up to position 3 in the inventive [(2Z,4E)-3-methyl-5-(2,6,6-trimethylcyclohexen-1-yl)penta-2,4-dienyl]triphenylphosphonium salt.

Carotenoids in the context of this disclosure are an extensive class of natural dies which cause a yellow to reddish, occasionally also blue color, and are formed essentially from an unsaturated hydrocarbon which is formed from isoprene units and has a conjugated π-electron system of double bonds, at least one of which has cis or Z conformation.

In particular, the use of compounds of the general formula 1 obtained by the process for preparation of 9Z-β-carotene is envisaged. The invention further provides for use of said compound 1 for preparation of phytohormones. Particular preference is given here to the use of compound 1 for preparation of carlactone.

A further essential part of the invention is the use of compounds of the general formula 1 for preparation of the active pharmaceutical ingredient 9Z-retinoic acid, also referred to as a pharmaceutically acceptable substance. This active pharmaceutical ingredient has to meet specific biocompatibility and purity requirements according to the current European Pharmacopeia, 7th edition, and according to good manufacturing practices GMP. This disclosure further provides for the use of compounds of the general formula 1 for preparation of pharmaceutically acceptable salts of 9Z-retinoic acid, and for preparation of pharmaceutically acceptable hydrolyzable esters of 9Z-retinoic acid. A further continuation comprises the use of the compound of the general formula 1 for preparation of metabolites of 9Z-retinoic acid as an active pharmaceutical ingredient.

The disclosure further provides for the use of compounds of the general formula 1 for preparation of retinoids for a formulation selected from the group consisting of tablets, capsules, pills, sachets, ointments, creams and lotions.

Yet another aspect of the invention, finally, comprises the use of compounds of the general formula 1 for preparation of retinoids for formulations for topical or oral use, especially for treatment of skin disorders, including preferably hand eczema or Karposi's sarcoma.

Further features, details and advantages of the invention are evident from the wording of the claims, and from the description of working examples which follows.

EXAMPLE 1

Isomerization of [(2E,4E)-3-methyl-5-(2,6,6-trimethylcyclohexen-1-yl)penta-2,4-dienyl]-triphenylphosphonium hydrogensulfate A 4000 ml round-bottom flask is initially charged with 2535 g (1.67 mol) of a 37.2% by weight solution of [(2E,4E)-3-methyl-5-(2,6,6-trimethylcyclohexen-1-yl)penta-2,4-dienyl]triphenylphosphonium hydrogensulfate in methanol under nitrogen, which is alkalized by addition of 111.30 g (0.618 mol) of a 30% by weight sodium methoxide solution in methanol, and the precipitated sodium sulfate is filtered off. The filtrate is pumped through a flow reactor heated to 145° C. with an exactly fixed residence time of 25 min. Subsequently, the solvent is distilled off, the residue is taken up in isopropanol and acidified with sulfuric acid to a pH of 0.3, and the unisomerized [(2E,4E)-3-methyl-5-(2,6,6-trimethylcyclohexen-1-yl)penta-2,4-dienyl]triphenylphosphonium salt of the general formula 2 is crystallized by adding 823 g of heptane and cooling to −10° C. After the crystals have been filtered off, 1648 g of an 11.2% by weight solution of [(2Z,4E)-3-methyl-5-(2,6,6-trimethylcyclohexen-1-yl)penta-2,4-dienyl]triphenylphosphonium-hydrogensulfate (0.327 mol) are obtained in a purity of 95% and a yield of 20%.

EXAMPLES 2 TO 5

Isomerization of [(2E,4E)-3-methyl-5-(2,6,6-trimethylcyclohexen-1-yl)penta-2,4-dienyl]triphenylphosphonium chloride at Various Temperatures 1 g of the aforementioned phosphonium salt is suspended in 10 ml of propyl acetate at 20° C. and heated in a microwave reactor to the temperatures listed in table 1 for 15 min. Subsequently, a sample is taken from the solution obtained, and separated by HPLC chromatography in a manner known in the art, and the areas determined for the individual peaks obtained in the chromatograph are used to determine the isomer ratios.

TABLE 1

| Example | T (° C.) | Compound of the general formula 2 with chloride as the anion | Compound of the general formula 1 with chloride as the anion | Further unidentified isomer A | Further unidentified isomer B |
| --- | --- | --- | --- | --- | --- |
| 2 | 140 | 58.04 | 23.54 | 3.86 | 2.84 |
| 3 | 150 | 53.85 | 24.88 | 5.63 | 3.83 |
| 4 | 160 | 50.37 | 23.02 | 6.65 | 4.74 |
| 5 | 170 | 48.70 | 23.80 | 10.21 | 3.49 |

It can be seen that the best yields are achieved at a temperature of 150° C.

EXAMPLES 6 TO 8

Isomerization of [(2E,4E)-3-methyl-5-(2,6,6-trimethylcyclohexen-1-yl)penta-2,4-dienyl]triphenylphosphonium chloride at 160° C. with Various Exactly Fixed Residence Times 1 g of the aforementioned phosphonium salt is suspended in 10 ml of propyl acetate at 20° C. and heated to 160° C. in a microwave reactor for different exactly fixed residence times stated in table 2. Subsequently, a sample is taken from the solution obtained and separated by HPLC chromatography in a manner familiar to those skilled in the art, and the areas determined for the individual peaks obtained in the chromatogram are used to determine the isomer ratio.

TABLE 2

| Example | T (° C.) | Compound of the general formula 2 with chloride as the anion | Compound of the general formula 1 with chloride as the anion | Further unidentified isomer A | Further unidentified isomer B |
| --- | --- | --- | --- | --- | --- |
| 6 | 5 | 58.78 | 22.74 | 4.09 | 3.04 |
| 7 | 10 | 53.18 | 23.12 | 5.9 | 4.14 |
| 8 | 15 | 50.37 | 23.02 | 6.65 | 4.74 |

It can be seen that the best yields are achieved with an exactly fixed residence time of 10 min.

EXAMPLES 9 TO 10

Isomerization of [(2E,4E)-3-methyl-5-(2,6,6-trimethylcyclohexen-1-yl)penta-2,4-dienyl]triphenylphosphonium tosylate at 160 and 180° C.

1 g of the aforementioned phosphonium salt is suspended in 10 ml of ethyl acetate at 20° C. and heated to the temperature listed in table 3 in a microwave reactor for 10 min. Subsequently, the isomer ratio of the solution obtained is determined by HPLC in the manner described in the preceding examples.

TABLE 3

| Examples | T (° C.) | Compound of the general formula 2 with tosylate as the anion | Compound of the general formula 1 with tosylate as the anion | Further unidentified isomer A | Further unidentified isomer B |
|---|---|---|---|---|---|
| 9 | 160 | 74.84 | 20.43 | 0.91 | 0.58 |
| 10 | 180 | 57.34 | 30.93 | 4.86 | 3.07 |

It can be seen that compounds of the general formula 1 with tosylate as the anion can be converted at higher temperatures than the corresponding chlorides, but also give higher yields compared to the corresponding chlorides at high temperatures.

It is a feature common to all compounds used for the inventive isomerization process that they do not decompose at temperatures above 100° C. Even at 180° C., no decomposition was observed.

The invention is not restricted to the embodiments given in the description including the examples and in the claims, but can be modified in various ways. It is thus also possible to isomerize all-E-configured olefinically unsaturated phosphonium salts having at least two olefinic double bonds and having large organic anions to corresponding Z,E compounds by the process according to the invention. The same applies to all-E-configured olefinically unsaturated phosphine compounds having at least two olefinic double bonds. In addition, olefinically unsaturated phosphonium salts having at least two olefinic double bonds each having Z conformation, or those having a 2E,4Z conformation, are isomerizable by the process according to the invention to the corresponding 2Z,4E-phosphonium salt, if required with addition of appropriate seed crystals of the target compound during or after the isomerization reaction.

It can be seen from all of this that the present invention relates to a process for preparing an olefinically unsaturated phosphonium salt having at least two olefinic double bonds, of which one double bond has Z or cis conformation and the second or another double bond has E conformation, from an olefinically unsaturated phosphonium salt having at least two olefinic double bonds which are of different configuration compared to the target compound, and especially both have an all-E or all-trans conformation. The invention further provides for the use of the compound obtained by the invention for provision of terpenoid substances as medicaments.

The invention claimed is:

1. A process for preparing [(2Z,4E)-3-methyl-5-(2,6,6-trimethylcyclohexen-1-yl)penta-2,4-dienyl]triphenylphosphonium salt of the general formula (1)

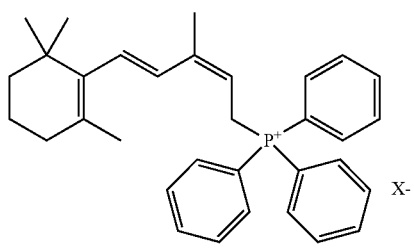

1 by isomerizing [(2E,4E)-3-methyl-5-(2,6,6-trimethylcyclohexen-1-yl)penta-2,4-dienyl]-triphenylphosphonium salt of the general formula (2),

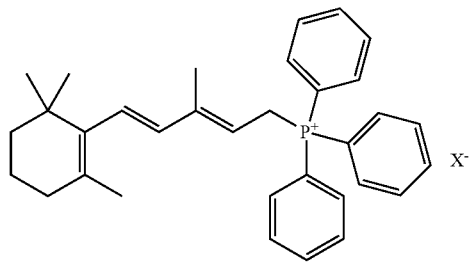

2 where the molar mass of the anion X⁻ is not more than 200 g/mol; and
wherein the isomerization is a thermal isomerization performed by heating within a temperature range from 50 to 200° C.

2. The process according to claim 1, wherein X⁻ is selected from the group consisting of halide, dihydrogenphosphate, nitrate, hydrogensulfate, sulfate, chlorate, perchlorate, tetrafluoroborate, C1-C4-alkanoates, and C1-C7-sulfonates.

3. The process according to claim 1, wherein the thermal isomerization is performed within a temperature range from 100° C. to 180° C.

4. The process according to claim 1, wherein the thermal isomerization is performed within a temperature range from 120° C. to 180° C.

5. The process according to claim 1, wherein the isomerization is performed within a pressure range from 1 to 100 bar.

6. The process according to claim 5, wherein the isomerization is performed within a pressure range from 5 to 80 bar.

7. The process according to claim 5, wherein the isomerization is performed within a pressure range from 8 to 50 bar.

8. The process according to claim 5, wherein the isomerization is performed within a pressure range from 10 to 25 bar.

9. The process according to claim 1, wherein the isomerization is performed in a solvent or a solvent mixture.

10. The process according to claim 9, wherein the solvent or solvent mixture is selected from the group consisting of toluene, xylene, dioxane, THF, DMF, DMSO, C1-C6-alcohol, C3-C7-ketone, ethyl acetate, propyl acetate, butyl acetate, ethyl propionate, and mixtures of at least two of these compounds.

11. The process according to claim 9, wherein the solvent used is methanol.

12. The process according to claim 1, wherein the isomerization is performed in the presence of a base.

13. The process according to claim 12, wherein the base is added in such an amount that the anions formed therefrom are 0.1 to 1 molar equivalent based on compound (2).

14. The process according to claim 13, wherein the base is added in such an amount that the anions formed therefrom are 0.2 to 0.7 molar equivalent based on compound (2).

15. The process according to claim 13, wherein the base is added in such an amount that the anions formed therefrom are 0.25 to 0.5 molar equivalent based on compound (2).

16. The process according to claim 1, wherein the isomerization is performed in a reactor with a fixed temperature profile and an exactly fixed residence time.

17. The process according to claim 16, wherein the reactor used is a microwave reactor or a flow tube reactor.

18. The process according to claim 1, wherein the isomerization is followed by removal and recycling of any unreacted starting material of the general formula (2).

19. The process according to claim 12, wherein the isomerization in the presence of base is followed by
exchanging the solvent present or the solvent mixture for an alcohol,
acidifying with an acid to a pH of 0 to 2,
adding a hydrocarbon liquid at room temperature,
cooling to a temperature in the range from −30° C. to 20° C.,
incubating at this temperature
and removing the solids obtained.

20. A process for preparing [(2Z,4E)-3-methyl-5-(2,6,6-trimethylcyclohexen-1-yl)penta-2,4-dienyl]triphenylphosphonium salt of the general formula (1)

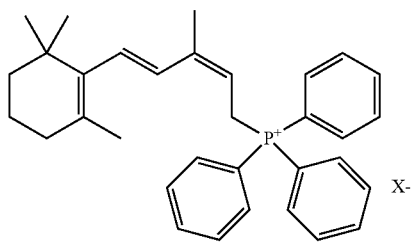

by isomerizing pure, well-characterized solid [(2E,4E)-3-methyl-5-(2,6,6-trimethylcyclohexen-1-yl)penta-2,4-dienyl]triphenylphosphonium salt of the general formula (2),

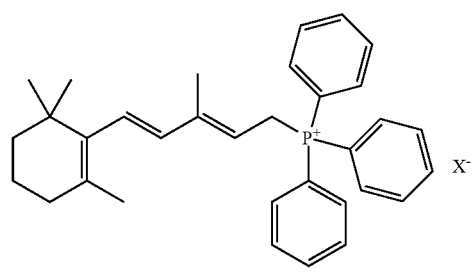

where the molar mass of the anion $X^-$ is not more than 200 g/mol; and wherein the isomerization is a thermal isomerization performed by heating within a temperature range from 50 to 200° C.

21. The process according to claim 20, wherein the isomerization is performed in the presence of a base in such an amount that the anions formed therefrom are 0.1 to 1 molar equivalent based on compound (2).

* * * * *